(12) United States Patent
Thornton et al.

(10) Patent No.: US 7,992,558 B2
(45) Date of Patent: Aug. 9, 2011

(54) STABILITY MEDICAL MASK

(75) Inventors: W. Keith Thornton, Dallas, TX (US); Annelise Thornton, Dallas, TX (US)

(73) Assignee: AirWay Technologies LLC, Carrollton, TX (US)

( * ) Notice: Subject to any disclaimer, the term of this patent is extended or adjusted under 35 U.S.C. 154(b) by 983 days.

(21) Appl. No.: 11/853,343

(22) Filed: Sep. 11, 2007

(65) Prior Publication Data
US 2008/0060648 A1   Mar. 13, 2008

Related U.S. Application Data

(60) Provisional application No. 60/825,243, filed on Sep. 11, 2006.

(51) Int. Cl.
*A62B 18/08* (2006.01)
*A62B 18/02* (2006.01)

(52) U.S. Cl. ......... 128/206.24; 128/205.25; 128/206.21; 128/207.11

(58) Field of Classification Search ............. 128/201.22, 128/201.23, 205.25, 206.21, 206.23–206.27, 128/207.11
See application file for complete search history.

(56) References Cited

U.S. PATENT DOCUMENTS

| | | |
|---|---|---|
| 339,334 A | 4/1886 | Searle |
| 690,663 A | 1/1902 | Pratt |
| 746,869 A | 12/1903 | Moulton |
| 774,446 A | 11/1904 | Moulton |
| 781,516 A | 1/1905 | Guthrie, Jr. |
| 885,196 A | 4/1908 | Steil |
| 893,213 A | 7/1908 | Whiteway |
| 911,476 A | 2/1909 | Cheesman ............... 128/206.12 |
| 996,783 A | 7/1911 | Moreau |
| 1,077,272 A | 11/1913 | Graybill et al. .......... 128/206.15 |
| 1,483,694 A | 2/1924 | Stukey |
| 1,675,202 A | 6/1928 | Warne |
| 1,679,748 A | 8/1928 | Stratton |
| 2,178,128 A | 10/1939 | Waite ............................ 128/136 |
| 2,383,649 A | 8/1945 | Heidbrink .................... 128/142 |
| 2,387,522 A | 10/1945 | Maurer .................... 128/201.15 |
| 2,424,533 A | 7/1947 | Faires .......................... 128/136 |

(Continued)

FOREIGN PATENT DOCUMENTS

DE        156627        12/1904

(Continued)

OTHER PUBLICATIONS

Mayo Clinic Health Letter; Reliable Information for a Healthier Life; *Snoring: Laser Surgery Joins Battle to Restore Peace and Quiet*; vol. 13, No. 7, 8 pages, Jul. 1995.

(Continued)

*Primary Examiner* — Kristen C Matter
(74) *Attorney, Agent, or Firm* — Baker Botts L.L.P.

(57) ABSTRACT

According to one embodiment, a medical mask includes a rigid sealing portion configured to cover and seal around at least a portion of a user's nose including the user's nostrils and a rigid stabilizing frame coupled to the rigid sealing portion. The rigid stabilizing frame includes a generally horizontal upper support member configured to bear against the user's forehead, a generally vertical support member coupled between the rigid sealing portion and the upper support member, and lower left and right support members coupled between the rigid sealing portion and the upper support member and configured to bear against the user's cheeks. The rigid stabilizing frame defines two openings configured to allow the user to see through the medical mask when the medical mask is positioned on the user's face.

19 Claims, 3 Drawing Sheets

U.S. PATENT DOCUMENTS

| | | | | |
|---|---|---|---|---|
| 2,505,028 A | 4/1950 | Boeger | | 128/215 |
| 2,521,084 A | 9/1950 | Oberto | | 128/141 |
| 2,574,623 A | 11/1951 | Clyde | | 128/136 |
| 2,627,268 A | 2/1953 | Leppich | | 128/136 |
| 2,671,446 A | 3/1954 | Mann | | 128/163 |
| 2,867,212 A | 1/1959 | Nunn, Jr. | | 128/136 |
| 2,882,893 A | 4/1959 | Godfroy | | 128/136 |
| 2,917,045 A | 12/1959 | Schildknecht et al. | | 128/141 |
| 2,922,418 A | 1/1960 | Heffernan et al. | | 128/206.15 |
| 2,977,636 A | 4/1961 | McGuire | | 18/58.7 |
| 3,037,501 A | 6/1962 | Miller | | 128/141 |
| 3,330,274 A | 7/1967 | Bennett | | 128/146.7 |
| 3,658,058 A | 4/1972 | Neidhart et al. | | 128/147 |
| 3,695,265 A | 10/1972 | Brevik | | 128/146.2 |
| 3,845,768 A | 11/1974 | Garrahan | | 128/142.7 |
| 4,050,457 A | 9/1977 | Davidson | | 128/145.5 |
| 4,233,972 A | 11/1980 | Hauff et al. | | 128/205.12 |
| 4,289,127 A | 9/1981 | Nelson | | 128/207.14 |
| 4,294,243 A | 10/1981 | Ernsting et al. | | 128/201.18 |
| 4,345,592 A | 8/1982 | Giorgini et al. | | 128/204.26 |
| 4,345,593 A | 8/1982 | Sullivan | | 128/204.26 |
| 4,392,490 A | 7/1983 | Mattingly et al. | | 128/202.27 |
| 4,397,701 A | 8/1983 | Johnson et al. | | 156/62 |
| 4,454,090 A | 6/1984 | Saumell | | 264/154 |
| 4,470,413 A | 9/1984 | Warncke | | 128/201.18 |
| 4,655,213 A | 4/1987 | Rapoport et al. | | 128/205.25 |
| 4,706,683 A | 11/1987 | Chilton et al. | | 128/654 |
| 4,784,123 A | 11/1988 | Robeson | | 128/90 |
| 4,796,621 A | 1/1989 | Barle et al. | | 128/206.23 |
| 4,858,606 A | 8/1989 | Hamlin | | 128/204.29 |
| 4,862,903 A | 9/1989 | Campbell | | 128/861 |
| 4,870,962 A | 10/1989 | Sitnik | | 128/205.13 |
| 4,886,056 A | 12/1989 | Simpson | | 128/201.25 |
| 4,906,234 A | 3/1990 | Voychehovski | | 604/79 |
| 4,919,128 A | 4/1990 | Kopala et al. | | 128/207.18 |
| 4,941,212 A | 7/1990 | Liff | | 2/206 |
| 5,042,478 A | 8/1991 | Kopala et al. | | 128/207.18 |
| 5,062,421 A | 11/1991 | Burns et al. | | 128/205.27 |
| 5,065,756 A | 11/1991 | Rapoport | | 128/204.18 |
| 5,066,231 A | 11/1991 | Oxman et al. | | 433/214 |
| 5,193,532 A | 3/1993 | Moa et al. | | 128/204.25 |
| 5,233,978 A | 8/1993 | Callaway | | 128/205.25 |
| 5,243,971 A | 9/1993 | Sullivan et al. | | 128/205.25 |
| 5,245,995 A | 9/1993 | Sullivan et al. | | 128/204.23 |
| 5,267,557 A | 12/1993 | Her-Mou | | 128/206.21 |
| 5,392,773 A | 2/1995 | Bertrand | | 128/206.11 |
| 5,456,264 A | 10/1995 | Series et al. | | 128/725 |
| 5,458,137 A | 10/1995 | Axe et al. | | 128/204.23 |
| 5,477,850 A | 12/1995 | Zegler et al. | | 128/202.11 |
| 5,503,146 A | 4/1996 | Froehlich et al. | | 128/204.23 |
| 5,517,983 A | 5/1996 | Deighan et al. | | 128/204.23 |
| 5,537,994 A | 7/1996 | Thornton | | 128/204.18 |
| 5,537,999 A | 7/1996 | Dearman et al. | | 128/205.25 |
| 5,538,000 A | 7/1996 | Rudolph | | 128/206.25 |
| 5,538,014 A | 7/1996 | Wilson et al. | | 128/863 |
| 5,540,223 A | 7/1996 | Starr et al. | | 128/205.25 |
| 5,551,419 A | 9/1996 | Froehlich et al. | | 128/204.23 |
| 5,558,090 A | 9/1996 | James | | 128/207.18 |
| RE35,339 E | 10/1996 | Rapoport | | 128/204.18 |
| 5,560,354 A | 10/1996 | Berthon-Jones et al. | | 128/205.25 |
| 5,592,935 A | 1/1997 | Elstran et al. | | 128/205.29 |
| 5,611,485 A | 3/1997 | Davis | | 239/8 |
| 5,657,751 A | 8/1997 | Karr, Jr. | | 128/205.18 |
| 5,657,752 A | 8/1997 | Landis et al. | | 128/207.13 |
| 5,662,101 A | 9/1997 | Ogden et al. | | 128/205.25 |
| 5,676,133 A | 10/1997 | Hickle et al. | | 128/205.12 |
| 5,687,715 A | 11/1997 | Landis et al. | | 128/207.18 |
| 5,713,349 A | 2/1998 | Keaney | | 128/204.23 |
| 5,718,244 A | 2/1998 | Thornton | | 128/864 |
| 5,718,500 A | 2/1998 | Vinci guera et al. | | 2/431 |
| 5,720,280 A | 2/1998 | Elstran et al. | | 128/205.25 |
| 5,724,965 A | 3/1998 | Handke et al. | | 128/207.13 |
| 5,746,201 A | 5/1998 | Kidd | | 128/206.24 |
| 5,752,510 A | 5/1998 | Goldstein | | 128/207.18 |
| 5,807,100 A | 9/1998 | Thornton | | 433/48 |
| 5,810,749 A | 9/1998 | Maas | | 602/6 |
| 5,832,918 A | 11/1998 | Pantino | | 128/205.25 |
| 5,846,082 A | 12/1998 | Thornton | | 433/215 |
| 5,887,587 A | 3/1999 | Groenke | | 128/207.13 |
| 5,954,048 A | 9/1999 | Thornton | | 128/201.18 |
| 5,983,892 A | 11/1999 | Thornton | | 128/201.26 |
| 5,988,166 A | 11/1999 | Hayek | | 128/205.26 |
| 6,012,455 A | 1/2000 | Goldstein | | 128/207.18 |
| 6,044,844 A | 4/2000 | Kwok et al. | | 128/207.11 |
| 6,083,442 A | 7/2000 | Gabilly | | 264/163 |
| 6,119,694 A | 9/2000 | Correa et al. | | 128/207.13 |
| 6,123,071 A | 9/2000 | Berthon-Jones et al. | | 128/204.18 |
| 6,209,542 B1 | 4/2001 | Thornton | | 128/206.29 |
| 6,263,871 B1 | 7/2001 | Brown et al. | | 128/200.29 |
| D448,473 S | 9/2001 | Barnett et al. | | D24/110.1 |
| 6,374,824 B1 | 4/2002 | Thornton | | 128/201.26 |
| 6,405,729 B1 | 6/2002 | Thornton | | 128/848 |
| 6,412,488 B1 | 7/2002 | Barnett et al. | | 128/207.13 |
| 6,464,924 B1 | 10/2002 | Thornton | | 264/331.12 |
| 6,494,206 B1 | 12/2002 | Bergamaschi et al. | | 128/206.24 |
| 6,520,177 B1 | 2/2003 | Bonhomme et al. | | 128/201.28 |
| 6,571,798 B1 | 6/2003 | Thornton | | 128/206.21 |
| 6,645,413 B2 | 11/2003 | Jacobs | | 264/222 |
| 6,675,802 B1 | 1/2004 | Thornton | | 128/206.29 |
| 6,857,428 B2 | 2/2005 | Thornton | | 128/206.21 |
| 6,877,513 B2 | 4/2005 | Scarberry et al. | | 128/848 |
| 7,036,508 B2 | 5/2006 | Kwok | | 128/207.11 |
| 7,077,138 B2 | 7/2006 | Bateman et al. | | 128/206.14 |
| 7,255,811 B2 | 8/2007 | Hirschmann et al. | | 252/299.01 |
| 2002/0129818 A1 | 9/2002 | Morgan et al. | | 128/206.26 |
| 2004/0237965 A1 | 12/2004 | Bibi et al. | | 128/206.29 |
| 2005/0016544 A1 | 1/2005 | Thornton | | 128/207.18 |
| 2005/0061324 A1 | 3/2005 | Tadros | | 128/205.25 |
| 2006/0005837 A1 | 1/2006 | Thornton | | 128/205.25 |
| 2006/0124131 A1 | 6/2006 | Chandran et al. | | 128/206.28 |
| 2007/0006879 A1 | 1/2007 | Thornton | | 128/203.29 |
| 2007/0163594 A1 | 7/2007 | Ho et al. | | 128/206.24 |
| 2008/0006273 A1 | 1/2008 | Thornton | | 128/206.21 |
| 2008/0006274 A1 | 1/2008 | Thornton | | 128/206.21 |
| 2008/0041390 A1 | 2/2008 | Radney | | 128/207.11 |
| 2008/0060648 A1 | 3/2008 | Thornton et al. | | 128/206.25 |

FOREIGN PATENT DOCUMENTS

| | | |
|---|---|---|
| DE | 35 43 931 A1 | 6/1987 |
| DE | 37 07 952 A1 | 9/1988 |
| DE | 37 19 009 A1 | 12/1988 |
| DE | 44 38 512 A1 | 5/1996 |
| DE | 198 46 686 A1 | 7/1999 |
| FR | 2 658 725 A1 | 8/1991 |
| FR | 2 731 624 A1 | 9/1996 |
| FR | 2731624 | 9/1996 |
| WO | WO 97/25010 | 7/1997 |
| WO | WO 98/20924 | 5/1998 |
| WO | WO 98/46177 | 10/1998 |

OTHER PUBLICATIONS

Schmidt-Nowara, et al.; An American Sleep Disorders Association Review; *Oral Appliances for the Treatment of Snoring and Obstructive Sleep Apnea: A Review*; pp. 501-510, 1995.

CPAP-PRO—Introducing A New Comfort Level for CPAP Users brochure, 2 pages.

"Donning the Mask," Dräger: X-plore 5500.2006.Dräger Safety, http://www.draeger-usa.com/ST/internet/pdf/US/protection/AnlegiPO_X-plore_5500_US.pdf, 2 pages, Accessed Sep. 14, 2006.

PCT, Notification of Transmittal of the International Search Report and the Written Opinion of the International Searching Authority, or the Declaration, PCT/US06/26622, 11 pages, Date Mailed: Feb. 21, 2007.

Canadian Intellectual Property Office, Application No. 2,502,280, Applicant: W. Keith Thornton, 3 pages, dated Feb. 23, 2010.

European Patent Office Communication, Application No. 03 809 555.0-1257, Applicant: W. Keith Thornton, 4 pages, dated Aug. 7, 2009.

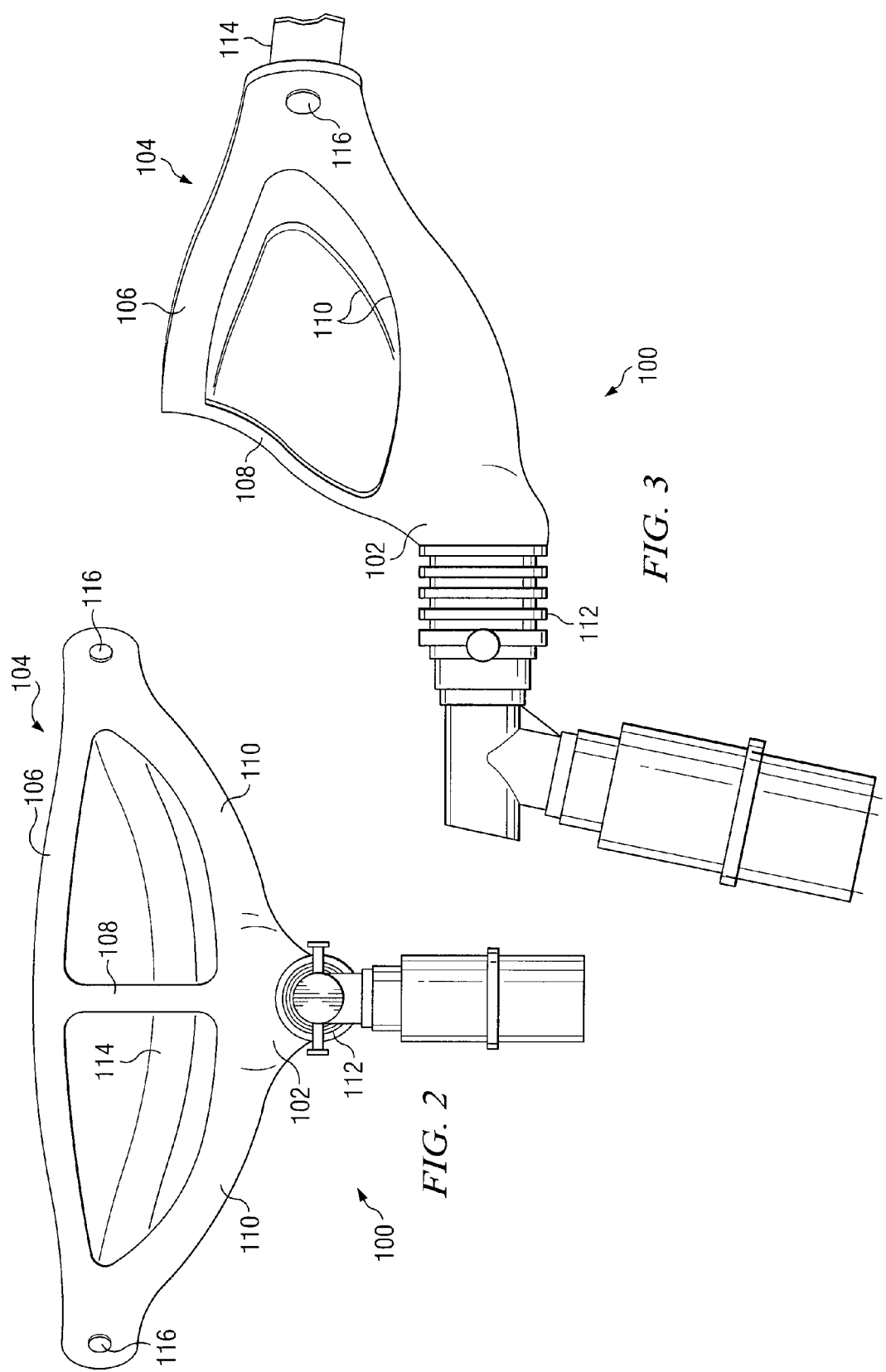

STABILITY MEDICAL MASK

RELATED APPLICATION

This application claims the benefit under 35 U.S.C. §119(e) of U.S. Provisional Application Ser. No. 60/825,243 filed Sep. 11, 2006.

TECHNICAL FIELD

This invention relates generally to masks for use in medical and other clinical applications, and more particularly to an improved stability medical mask.

BACKGROUND

Many people experience breathing problems on a recurring basis, which often result in sleep disordered breathing (i.e., difficulty sleeping, snoring, or other more serious conditions such as obstructive sleep apnea). Previous devices for improving a user's breathing have included face masks, nose masks, or nasal inserts that help deliver air to the user's nose at positive pressure. These devices help force open the user's breathing passage and thereby improve the user's breathing. However, previous devices have often provided an inadequate fit, been unstable, and been prone to movement when users are sleeping, and have often required multiple straps or other devices to hold them in place. Thus, previous devices have caused discomfort for users and have often failed to adequately prevent leakage.

Overview

According to one embodiment, a medical mask includes a rigid sealing portion configured to cover and seal around at least a portion of a user's nose including the user's nostrils and a rigid stabilizing frame coupled to the rigid sealing portion. The rigid stabilizing frame includes a generally horizontal upper support member configured to bear against the user's forehead, a generally vertical support member coupled between the rigid sealing portion and the upper support member, and lower left and right support members coupled between the rigid sealing portion and the upper support member and configured to bear against the user's cheeks. The rigid stabilizing frame defines two openings configured to allow the user to see through the medical mask when the medical mask is positioned on the user's face.

According to another embodiment, a method for forming a custom medical mask includes applying a thin sheet of deformable material against a portion of a user's face including at least a portion of the nose including the nostrils, at least a portion of the forehead, and at least a portion of the cheeks; deforming the thin sheet of deformable material against the portion of the user's face to cause the thin sheet of deformable material to conform to the user's face; allowing the thin sheet of deformable material to transition to a substantially rigid state; and removing a portion of the thin sheet of deformable material to form a custom medical mask. The custom medical mask includes a rigid sealing portion configured to cover and seal around at least a portion of the user's nose including the user's nostrils; and a rigid stabilizing frame coupled to the rigid sealing portion. The rigid stabilizing frame includes a generally horizontal upper support member configured to bear against the user's forehead, a generally vertical support member coupled between the rigid sealing portion and the upper support member, and lower left and right support members coupled between the rigid sealing portion and the upper support member and configured to bear against the user's cheeks. The rigid stabilizing frame defines two openings configured to allow the user to see through the medical mask when the medical mask is positioned on the user's face.

According to another embodiment, a custom medical mask includes a rigid sealing portion configured to cover and seal around at least a portion of a user's nose including the user's nostrils and a rigid stabilizing frame coupled to the rigid sealing portion. The rigid stabilizing frame includes a generally horizontal upper support member configured to bear against the user's forehead, a generally vertical support member coupled between the rigid sealing portion and the upper support member, and lower left and right support members coupled between the rigid sealing portion and the upper support member and configured to bear against the user's cheeks. The rigid stabilizing frame defines two openings configured to allow the user to see through the custom medical mask when the custom medical mask is positioned on the user's face. The rigid sealing portion and the rigid stabilizing frame are formed from a single, integral piece of material comprising a polycaprolactone polymer and custom-fitted to the user's unique facial features.

Certain embodiments may provide one or more technical advantages. Certain embodiments may provide a medical mask with improved stability. Certain embodiments may provide a custom medical mask that conforms substantially optimally to a user's unique facial features. Certain embodiments may provide a medical mask for delivering clinical gases to the nasal passages of a user that may be held in a stable location on the user's face through the use of a single strap. Certain embodiments may provide improved fit, increased comfort, reduced leakage, and improved performance, whether for treating sleep disordered breathing, administering anesthesia, or any other suitable purpose for which the medical mask is used. Certain embodiments may provide all, some, or none of these advantages. Certain embodiments may provide one or more other technical advantages, one or more of which may be apparent to those skilled in the art from the figures, descriptions, and claims included herein.

BRIEF DESCRIPTION OF THE DRAWINGS

For a more complete understanding of the present invention and certain of its advantages, reference is now made to the following description, taken in conjunction with the accompanying drawings, in which:

FIGS. 1 through 3 illustrate multiple views of an example medical mask; and

DESCRIPTION OF EXAMPLE EMBODIMENTS

Figure 1:
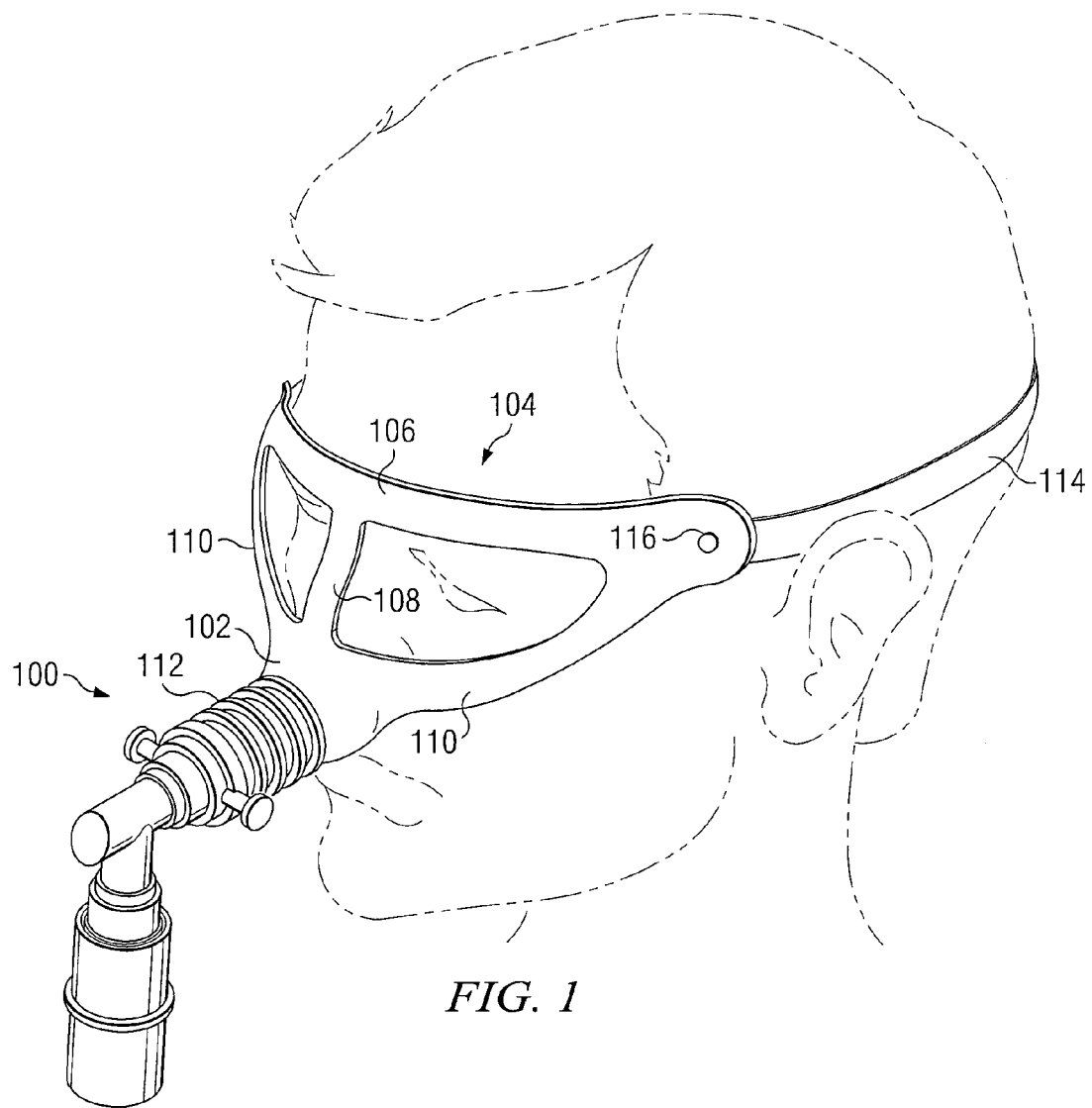

FIGS. 1 through 3 illustrate an example medical mask 100. Medical mask 100 includes sealing portion 102 and stabilizing frame 104. In certain embodiments, medical mask 100 may also include fitting 112 and/or strap 114. Sealing portion 102 is configured to cover and seal around at least a portion of a user's nose including the user's nostrils. In certain embodiments, the seal provided by sealing portion 102 may be a substantially air-tight seal and sealing portion 102 may be substantially rigid. In embodiments in which sealing portion 102 is substantially rigid, the rigidity of sealing portion 102 may improve the seal around the user's nose when a clinical gas is delivered to the user. For example, when a clinical gas is delivered to the user, it may cause the user's nose to inflate against sealing portion 102 to improve the seal.

In certain embodiments, stabilizing frame 104 includes upper support member 106, vertical support member 108, and lower left and right support members 110. In these embodiments, stabilizing frame 104 defines two openings configured to allow a user to see through medical mask 100 when medical mask 100 is positioned on the user's face. Upper support member 106 may be a generally horizontal support member configured to bear against at least a portion of a user's forehead. In certain embodiments, upper support member 106 spans all or substantially all of the width of the user's forehead. Vertical support member 108 may extend vertically between sealing portion 102 and upper support member 106. In certain embodiments, vertical support member 108 may be configured to bear against the rigid upper portion of the user's nose. Left and right support members 110 may be generally diagonal support members that extend between sealing portion 102 and upper support member 106 and are configured to bear against the user's cheeks. In certain embodiments, left and right support members 110 may be configured to bear against the rigid upper portions of the user's cheeks to the left and right of the user's nose.

Although in certain embodiments stabilizing frame 104 is continuous so as to define two fully-enclosed openings configured to allow a user to see through medical mask 100 when medical mask 100 is positioned on the user's face, in alternative embodiments one or more portions of stabilizing frame 104 may be eliminated or made discontinuous according to particular needs. For example, in certain embodiments, stabilizing frame 104 may not include vertical stabilizing member 108, or vertical support member may be discontinuous so as not to extend the entire distance between sealing portion 102 and upper support member 106, such that stabilizing frame 104 defines only a single opening to allow the user to see through medical mask 100 when medical mask 100 is positioned on the user's face. As another example, left and right support members 110 may be discontinuous, such that left and right support members 110 do not extend the entire distance between sealing portion 102 and upper support member 106. As another example, upper support member 106 may be discontinuous, such that upper support member 106 spans only a portion of the user's forehead and does not couple to left and right support members 110. The present invention contemplates any one or more of these alternatives, singly or in combination, according to particular needs.

In certain embodiments, stabilizing frame 104 may include attachment sites 116 to couple stabilizing frame 104 to strap 114. Stabilizing frame 104 may be coupled to strap 114 using buckles, rivets, snaps or any other appropriate technique.

In embodiments of medical mask 100 including fitting 112, fitting 112 may include any suitable structure to connect medical mask 100 to a clinical gas delivery system. For example, fitting 112 may represent an acrylic, male-type hose connector that couples to an opening in sealing portion 102. As another example, fitting 112 may represent a gasket surrounding an opening into sealing portion 102. Fitting 112 may include a structure configured to connect medical mask 100 to multiple hoses. A suitable clinical gas delivery system for use with medical mask 100 may be a Continuous Positive Airway Pressure (CPAP) system, a Bi-level Positive Airway Pressure (BiPAP) system, and/or a system configured to deliver an anesthetic, oxygen, and/or other appropriate clinical gas to a user wearing medical mask 100.

In operation, medical mask 100 may be positioned over the user's face such that sealing portion 102 is positioned over at least a portion of the user's nose and stabilizing frame 104 bears against a portion of the user's forehead and the user's cheeks. When medical mask 100 is coupled to a clinical gas delivery system through the use of fitting 112, sealing portion 102 may operate to assist in delivering a clinical gas to the user through the user's nasal passages. By bearing against portions of the user's forehead and the user's cheeks, stabilizing frame 104 may provide stability for medical mask 100 when medical mask 100 is worn. This improved stability may be due to the broad contact area of stabilizing frame 104 and/or to the rigid nature of the user's orbital rim, including portions of the user's forehead and cheeks. The improved stability provided by stabilizing frame 104 may serve to enhance the fit of medical mask 100 on the user's face, to increase the user's comfort when wearing medical mask 100, to reduce leakage of clinical gas, and/or to improve the performance of medical mask 100 when worn. In certain embodiments, medical mask 100 may be used for treating sleep-disordered breathing, for administering anesthesia, or for delivering a clinical gas to a user for any other suitable purpose.

Strap 114 may be used to assist in positioning and securing medical mask 100 on the user's face. Although, in alternative embodiments, any other appropriate securing means may be used to secure medical mask 100 on the user's face. In embodiments of medical mask 100 utilizing strap 114, stabilizing frame 104 may allow medical mask 100 to be held in a stable location on the user's face through the use of a single strap 114 that extends over the top of the user's ears and behind the user's head, as shown in FIG. 1.

In certain embodiments, sealing portion 102 and/or stabilizing portion 104 may be formed from a thin sheet of deformable material. In certain embodiments, sealing portion 102 and stabilizing frame 104 may be formed from a single, integral piece of material. In certain embodiments, medical mask 100 may include a suitable thermoplastic polymer and suitable fillers, stabilizers, coloring agents, antioxidants, antimicrobial agents, and/or other materials. In certain embodiments, medical mask 100 may include a light curing material such as the material sold under the name TRIAD by DENTSPLY INTERNATIONAL INC. Such materials are known in various contexts to those skilled in the art.

In a particular embodiment, medical mask 100 may include, possibly in addition to one or more other materials, one or more of the thermoplastic polycaprolactone polymers or other aliphatic polyesters described in U.S. Pat. Nos. 4,784, 123 and 5,112,225 and product literature of UNION CARBIDE CORPORATION. One or more polycaprolactone polymers may have the formula:

(1)

where R is an aliphatic hydrocarbon and n may range between approximately 300 to approximately 650. However, the present invention contemplates using any suitable polycaprolactone polymer.

For example, medical mask 100 may include one or more of the TONE P-700, TONE P-767, or TONE P-787 polycaprolactone polymers manufactured by UNION CARBIDE CORPORATION, singly or in any combination. In a particular example, medical mask 100 may include approximately thirty parts by volume of TONE P-700 and sixty parts by volume of TONE P-767, together with approximately ten parts by volume of one or more other polymers, depending upon the application and particular needs.

TONE polycaprolactone polymers are described in U.S. Pat. Nos. 4,784,123 and 5,112,225 and product literature of UNION CARBIDE CORPORATION as including homopolymers, block copolymers, graft copolymers, or other polymers containing epsilon-caprolactone. Polymerization may be initiated using a diol, for example and without limitation, ethylene glycol, diethylene glycol, neopentyl glycol, butane diol, hexane diol, or any other appropriate diol. The diol may have the formula:

$$HO-R-OH \quad (2)$$

where R is an aliphatic hydrocarbon. In general, polycaprolactone polymers may display desirable dimensional stability and thermoplasticity during cooling, biocompatibility, and a variety of other characteristics making them suitable for use in forming embodiments of medical mask 100.

Figure 4:
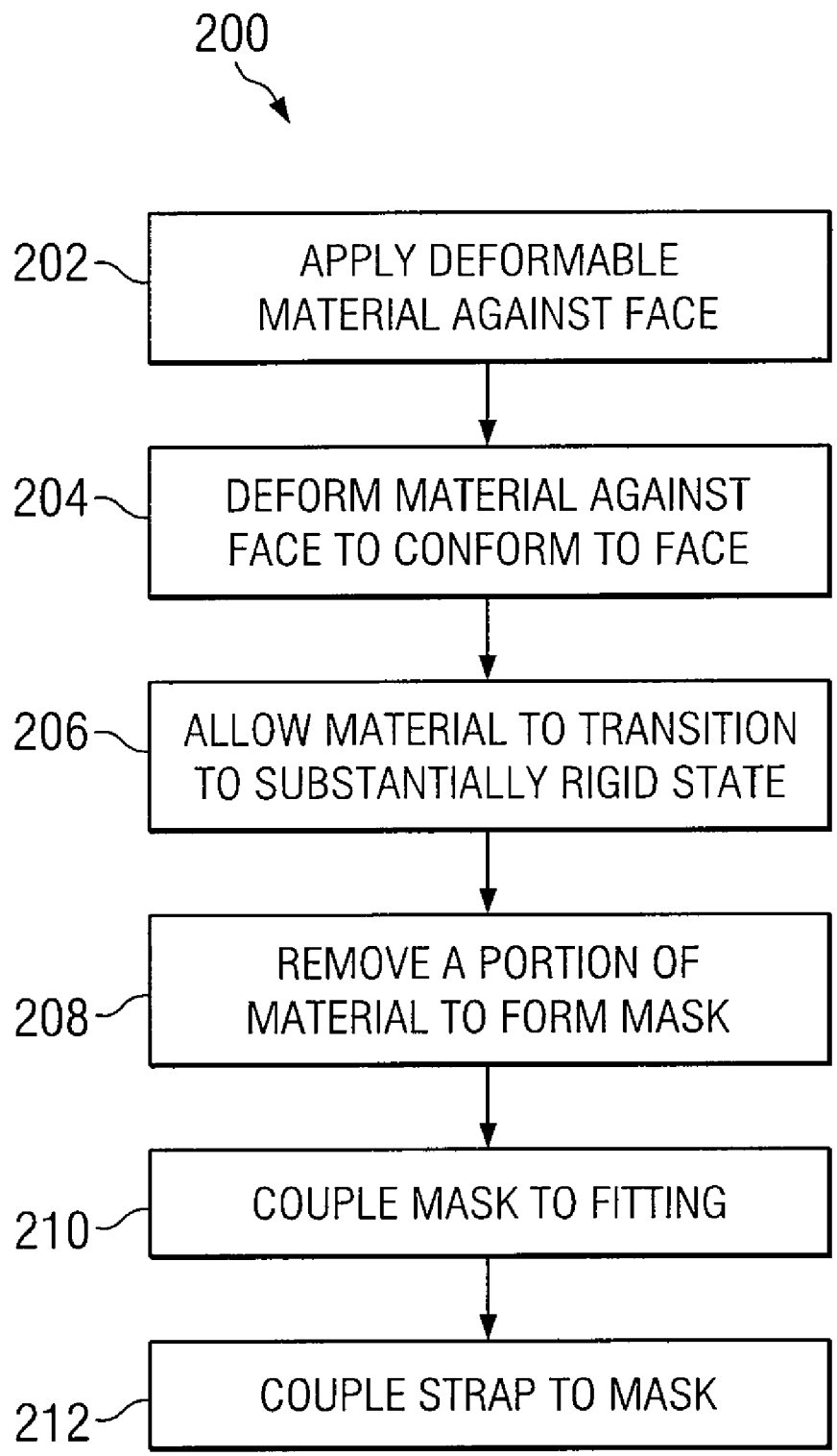
FIG. 4 is a flowchart illustrating an example method for forming an example medical mask.

FIG. 4 is a flowchart illustrating an example method 200 for forming an example medical mask 100. At step 202, a deformable material is applied against the user's face while the deformable material is in a deformable state. In certain embodiments, the deformable material may have been placed in a deformable state by heating the material. For example, where the deformable material includes one or more polycaprolactone polymers, the material may be heated in a microwave oven, in water or other non-solvent neutral liquid, or in any other suitable manner to between approximately 140° Fahrenheit and approximately 180° Fahrenheit, so as to place the material in a deformable state. At step 204, the deformable material is deformed against the user's face to conform to the user's face. In certain embodiments, by deforming the material against the user's face, the deformable material may be custom-fitted to the user's unique facial features. At step 206, the material is allowed to transition to a substantially rigid state. For example, the material may be allowed to cool and harden, so as to transition to a substantially rigid state and retain its deformed shape.

At step 208, a portion of the material is removed to form medical mask 100. For example, a portion of the material may be removed to define one or more openings to allow a user to see through medical mask 100 when medical mask 100 is positioned on the user's face. In certain embodiments, the portion of material may be removed prior to applying the material against the user's face. In certain embodiments, rather than removing a portion of the material, the material may be pre-formed with one or more openings or, alternatively, multiple pieces of deformable material may be applied to the user's face to define the one or more openings. In certain embodiments, in addition to the one or more openings to allow a user to see through medical mask 100, a portion of the material may be removed to define one or more openings to allow a clinical gas to be delivered to the user's nasal passages.

At step 210, for embodiments including fitting 112, fitting 112 is coupled to medical mask 100. In certain embodiments, fitting 112 may be coupled to medical mask 100 while the deformable material is still in a deformable state. In alternative embodiments, fitting 112 may be coupled to medical mask 100 after the material is allowed to transition to a substantially rigid state. In certain embodiments, fitting 112 may be coupled to medical mask 100 through a chemical bonding process, through the use of one or more adhesives, through the application of additional deformable material, or in any other suitable manner. At step 212, in embodiments including strap 114, strap 114 is coupled to medical mask 100. While FIG. 4 illustrates one embodiment, various steps may be added or omitted without departing from the scope of the invention. In addition, some of the illustrated steps could be performed differently or in a different order without departing from the scope of the invention.

In certain embodiments, all or a portion of medical mask 100 may be formed from a three-dimensional electronic model, such as is described in U.S. Patent Application Ser. No. 60/806,657, filed on Jul. 6, 2006 and incorporated herein by reference. For example, sealing portion 102, stabilizing frame 104, and fitting 112 may be formed through a stereolithography process, such that fitting 112 may be integrally formed with sealing portion 102 and stabilizing frame 104.

Although the present invention has been described in several embodiments, a plenitude of changes, substitutions, variations, transformations, and modifications may be suggested to one skilled in the art, and it is intended that the present invention encompass such changes, substitutions, variations, transformations, and modifications as fall within the scope of the appended claims.

What is claimed is:

1. A medical mask, comprising:
a rigid sealing portion configured to cover and seal around at least a portion of a user's nose including the user's nostrils; and
a rigid stabilizing frame coupled to the rigid sealing portion and comprising:
a generally horizontal upper rigid support member configured to bear against the user's forehead;
a generally vertical rigid support member coupled between the rigid sealing portion and the upper support member; and
lower left and right rigid support members coupled between the rigid sealing portion and the upper support member and configured to bear against the user's cheeks;
the rigid stabilizing frame defining two openings configured to allow the user to see through the medical mask when the medical mask is positioned on the user's face.

2. The medical mask of claim 1, wherein the rigid sealing portion and the rigid stabilizing frame are custom-fitted to the user's unique facial features.

3. The medical mask of claim 1, wherein the rigid sealing portion and the rigid stabilizing frame are formed from a single, integral piece of material.

4. The medical mask of claim 1, wherein the rigid sealing portion and the rigid stabilizing frame each comprise a thermoplastic polymer.

5. The medical mask of claim 4, wherein the thermoplastic polymer comprises a polycaprolactone polymer.

6. The medical mask of claim 1, wherein the generally vertical support member is configured to bear against the bridge of the user's nose.

7. The medical mask of claim 1, further comprising a fitting configured to couple the medical mask to a clinical gas delivery system, the rigid sealing portion configured to provide a substantially airtight seal against the user's face during delivery of a clinical gas to the user through the fitting.

8. The medical mask of claim 1, further comprising a strap coupled to the rigid stabilizing portion at left and right attachment sites.

9. A method for forming a custom medical mask, comprising:
applying a thin sheet of deformable material against a portion of a user's face including at least a portion of the nose including the nostrils, at least a portion of the forehead, and at least a portion of the cheeks;

deforming the thin sheet of deformable material against the portion of the user's face to cause the thin sheet of deformable material to conform to the user's face;

allowing the thin sheet of deformable material to transition to a substantially rigid state; and removing a portion of the thin sheet of deformable material to form a custom medical mask comprising:

a rigid sealing portion configured to cover and seal around at least a portion of the user's nose including the user's nostrils; and a rigid stabilizing frame coupled to the rigid sealing portion and comprising:

a generally horizontal upper rigid support member configured to bear against the user's forehead;

a generally vertical rigid support member coupled between the rigid sealing portion and the upper support member; and lower left and right rigid support members coupled between the rigid sealing portion and the upper support member and configured to bear against the user's cheeks;

the rigid stabilizing frame defining two openings configured to allow the user to see through the medical mask when the medical mask is positioned on the user's face.

10. The method of claim 9, wherein the thin sheet of deformable material comprises a thermoplastic polymer.

11. The method of claim 10, wherein the thermoplastic polymer comprises a polycaprolactone polymer.

12. The method of claim 9, wherein the generally vertical support member is configured to bear against the bridge of the user's nose.

13. The method of claim 9, further comprising coupling the custom medical mask to a fitting configured to couple the custom medical mask to a clinical gas delivery system.

14. The method of claim 13, wherein the rigid sealing portion is configured to provide a substantially airtight seal against the user's face during delivery of a clinical gas to the user through the fitting.

15. The method of claim 9, further comprising coupling a strap to the rigid stabilizing portion at left and right attachment sites.

16. A custom medical mask, comprising:

a rigid sealing portion configured to cover and seal around at least a portion of a user's nose including the user's nostrils; and a rigid stabilizing frame coupled to the rigid sealing portion and comprising:

a generally horizontal upper rigid support member configured to bear against the user's forehead;

a generally vertical rigid support member coupled between the rigid sealing portion and the upper support member; and lower left and right rigid support members coupled between the rigid sealing portion and the upper support member and configured to bear against the user's cheeks;

the rigid stabilizing frame defining two openings configured to allow the user to see through the custom medical mask when the custom medical mask is positioned on the user's face;

the rigid sealing portion and the rigid stabilizing frame being formed from a single, integral piece of material comprising a polycaprolactone polymer and custom-fitted to the user's unique facial features.

17. The custom medical mask of claim 16, further comprising a strap coupled to the rigid stabilizing frame at left and right attachment sites and configured to hold the rigid sealing portion in position.

18. The custom medical mask of claim 16, wherein the generally vertical support member is configured to bear against the bridge of the user's nose.

19. The custom medical mask of claim 16, further comprising a fitting configured to couple the custom medical mask to a clinical gas delivery system, the rigid sealing portion configured to provide a substantially airtight seal against the user's face during delivery of a clinical gas to the user through the fitting.

* * * * *